Figure 1:
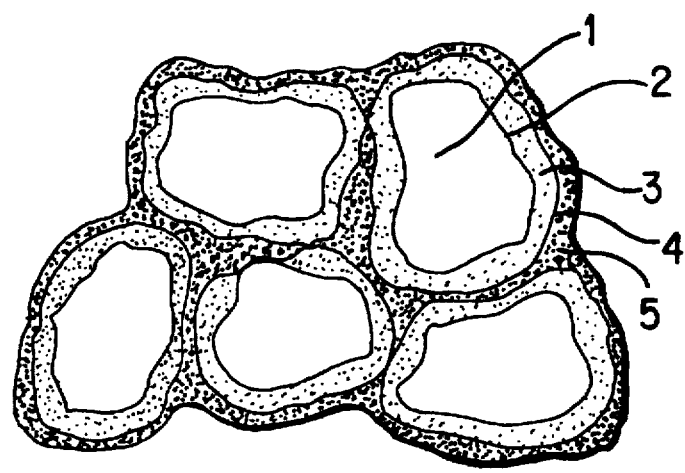
Figure 2:
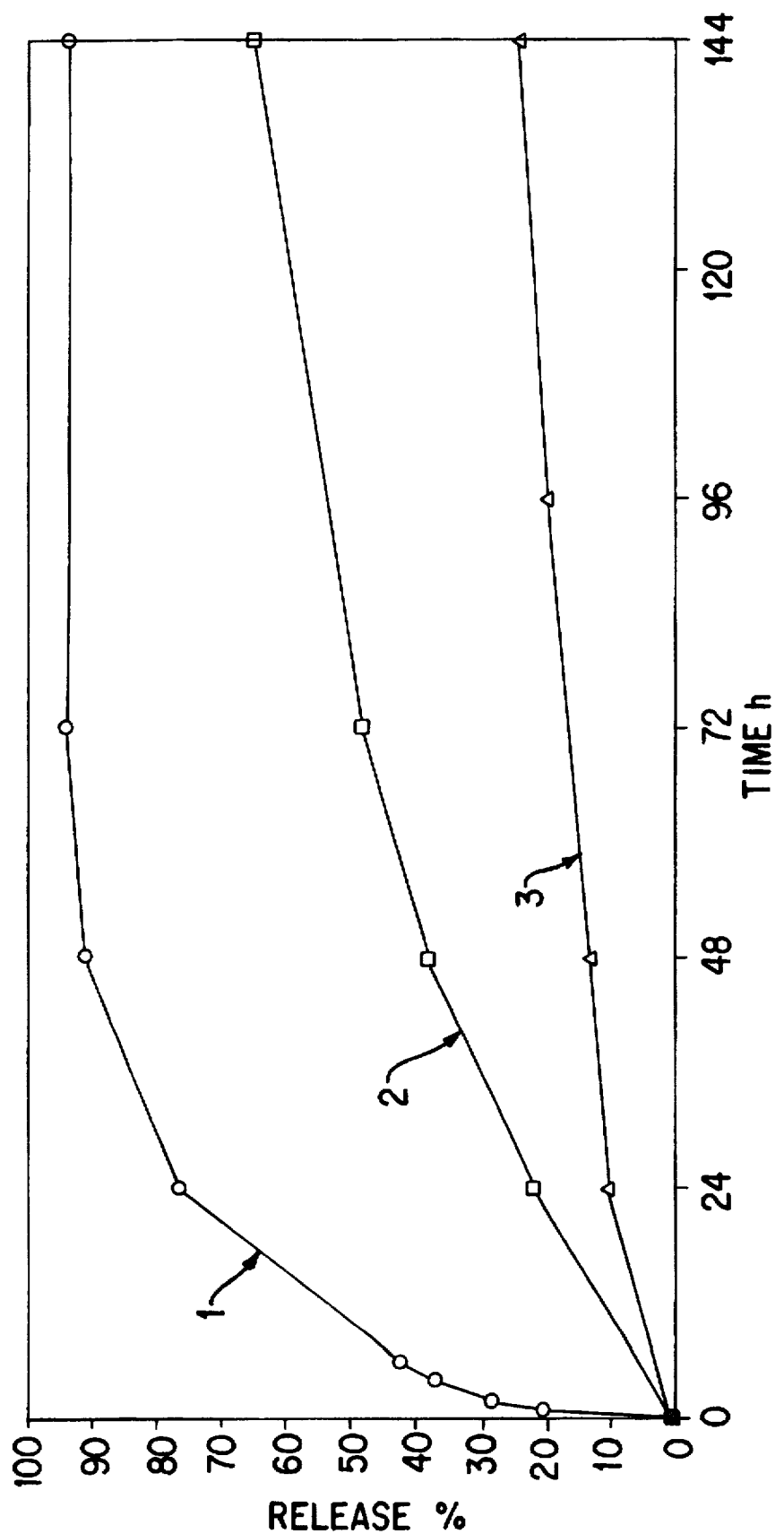

United States Patent [19]

Nastke et al.

[11] Patent Number: 5,788,991
[45] Date of Patent: Aug. 4, 1998

[54] COATED MICROPARTICLE AGGLOMERATES

[75] Inventors: Rudolf Nastke, Rehbrücke, Germany; Ernst Neuenschwander, Riehen, Switzerland; Andreas Leonhardt, Freiburg, Germany

[73] Assignee: Novartis Corporation, Summit, N.J.

[21] Appl. No.: 532,550
[22] PCT Filed: Mar. 21, 1994
[86] PCT No.: PCT/EP94/00881
   § 371 Date: Sep. 29, 1995
   § 102(e) Date: Sep. 29, 1995
[87] PCT Pub. No.: WO94/22303
   PCT Pub. Date: Oct. 13, 1994

[30] Foreign Application Priority Data

Apr. 1, 1993 [GB] United Kingdom ............ 9306808

[51] Int. Cl.⁶ .................. A61K 9/16; A61K 9/50
[52] U.S. Cl. .............. 424/490; 424/489; 424/405; 424/406; 424/409; 47/48.5
[58] Field of Search .................. 424/490, 489, 424/405, 406, 409; 47/48.5

[56] References Cited

U.S. PATENT DOCUMENTS

| | | | |
|---|---|---|---|
| 3,041,289 | 6/1962 | Katchen et al. | 252/316 |
| 4,891,172 | 1/1990 | Matsushita et al. | 264/433 |
| 4,938,797 | 7/1990 | Hässlin et al. | 71/118 |
| 5,335,449 | 8/1994 | Beatty | 47/48.5 |

FOREIGN PATENT DOCUMENTS

| | | |
|---|---|---|
| 0079668 | 8/1982 | European Pat. Off. . |
| 0532463 | 3/1993 | European Pat. Off. . |
| 3629714 | 3/1987 | Germany . |
| 1236885 | 6/1971 | United Kingdom . |
| 8300799 | 3/1983 | WIPO . |
| 9104661 | 4/1991 | WIPO . |

OTHER PUBLICATIONS

Chemical Abst. 107:213619y, Dietrich et al., p. 224, (1987).

*Primary Examiner*—Thurman K. Page
*Assistant Examiner*—William E. Benston, Jr.
*Attorney, Agent, or Firm*—Marla J. Mathias; William A. Teoli, Jr.

[57] ABSTRACT

One object of the invention, therefore, is to provide encapsulated biologically active solid microparticle agglomerates, each agglomerate comprising either I
 i) at least two closely associated microparticles, each microparticle being coated partially or completely by at least one discrete layer of a polymer, and
 ii) at least one outer discrete coating layer of the same polymer which envelops the coated microparticles to form an agglomerate of closely associated microparticles, or II
 i) a cluster of at least two closely associated microparticles, each microparticle being coated partially or completely by at least one layer of a polymer, the microparticles adhering together through the polymer to form said cluster, and
 ii) at least one outer discrete coating layer of the same polymer which envelops said cluster to form a discrete agglomerate, wherein in types I and II an inter-phase boundary is formed between each particle and the first coating layer, between individual coating layers and between the outer agglomerating envelope layer and the penultimate coating layer, and the total weight of polymer coating within and outside the agglomerate is no greater than 40% of the average agglomerate weight.

12 Claims, 2 Drawing Sheets

COATED MICROPARTICLE AGGLOMERATES

This application is a 371 of PCT/EP94/00881 filed Mar. 21, 1994.

The present invention relates to agglomerates of coated biologically active microparticles, a process for preparing such agglomerates and a method of using these agglomerates in sustained-release formulations.

Encapsulation techniques are known and described, for example, in U.S. Pat. No. 4,938,797. The processes known to coat solid particulate active substances suffer from a number of disadvantages: due to the irregular geometry of particulate matter, coating is usually incomplete and the user risks skin-contact with the active substance. Furthermore, the problems of non-linear and/or incomplete release include environmental damage due to residual active substance, and unpredictable efficacy rates.

Microencapsulated agricultural chemicals are described in published PCT application WO 91/04661. Microencapsulation by curing of a prepolymer may be accomplished in a single stage or in repeated stages. The polymer layers form a homogeneous coating which is a mono-coating since the repeated stages are carried out in the same reaction mixture by adding fresh hardener and/or prepolymer. The rate of release is rapid to begin with, but falls after an initial burst.

In EP patent application 0 079668 A1 granules are described comprising the pesticide in a solid core, such core then being coated with at least one layer of a particular membrane selected from the group of dienes and an unsaturated fatty acid radical. The application of plural layers is also described each layer increasing the thickness of the coating, but no discrete phase boundary being formed between each layer.

Minute encapsulated clusters of capsules are described in U.S. Pat. No. 3,041,289. A coacervation process is used to prepare the encapsulated clusters in which coating layers are deposited under changing pH conditions. A multiple component system is present in which micro-emulsions are used.

It is further known that the coating of microparticles using low-speed stirring results in the formation of agglomerates where the microparticles adhere together through the polymer coating. These agglomerates show undesirable release properties because a complete coating cannot be achieved.

There is a need for a more efficient and predictable sustained-release delivery system for biologically active substances. A particular need is found in agriculture where the release characteristics of granular pesticide delivery systems tend to comprise a strong initial burst, followed by an ever-diminishing rate of release of the active substance. A constant rate of release can be illustrated graphically by a linear relationship between time and the amount of active substance released.

Surprisingly it has now been found that much-improved sustained release rates of active substance can be achieved with agglomerates of microparticulate biologically active substances, the microparticles being coated by a polymeric material and the agglomerate being formed of a cluster of coated particles which is itself coated by the same polymeric material. There exist discrete phase boundaries between the particles and their coating layers, between the individual coating layers, and between the outer envelope layer(s) around the cluster and the particle coatings. It has been found that in this way, high initial release rates observed in the prior art can be suppressed. This is especially useful when the active substance is a pesticide. Moreover handling safety is improved, and a reduced amount of coating material is achieved while effecting complete coating.

One object of the invention, therefore, is to provide encapsulated biologically active solid microparticle agglomerates, each agglomerate comprising either I
  i) at least two closely associated microparticles, each microparticle being coated partially or completely by at least one discrete layer of a polymer, and
  ii) at least one outer discrete coating layer of the same polymer which envelops the coated microparticles to form an agglomerate of closely associated microparticles, or II
  i) a cluster of at least two closely associated microparticles, each microparticle being coated partially or completely by at least one layer of a polymer, the microparticles adhering together through the polymer to form said cluster, and
  ii) at least one outer discrete coating layer of the same polymer which envelops said cluster to form a discrete agglomerate, wherein in types I and II an inter-phase boundary is formed between each particle and the first coating layer, between individual coating layers and between the outer agglomerating envelope layer and the penultimate coating layer, and the total weight of polymer coating within and outside the agglomerate is no greater than 40% of the average agglomerate weight.

The agglomerates according to the invention consist of up to several thousand microparticles. Agglomerates of up to 1000 microparticles are preferred; more preferably the agglomerates contain up to 300 microparticles.

The median particle diameter can be between 3 and 2000 μm, preferably between 5 and 100 μm, and more preferably between 10 and 30 μm.

The weight of coating material around the microparticles and the agglomerate itself is preferably from 5 to 40%, more preferably 5 to 30% and particularly preferred from 10 to 20% of the agglomerate weight.

The agglomerates according to the invention consist of clusters of discrete singly-coated or multiply-coated microparticles, preferably singly-coated microparticles. Each agglomerate can itself be singly- or multiply-coated, but a single polymer coating layer is preferred.

The agglomerates of type I according to the invention are illustrated in FIG. 1.

In FIG. 1, region 1 represents the microparticulate active substance, regions 2 and 4 represent interphase boundaries, region 3 represents the first coating layer and region 5 represents a continuous layer enveloping the coated particles to form an agglomerate. Region 2 represents the interphase boundary between the particle and first coating layer (3), and region 4 represents the interphase boundary between the coating layer (3) and the outer continuous layer (5).

The discrete phase-boundary surface between each coating layer can be identified by known surface-analysis methods, for example electron microscopy.

The active substance represents at least 60%, preferably from 60 to 95%, and more preferably 70 to 95% by weight of the coated agglomerate. Particularly preferred is 80 to 90% by weight active substance.

The biologically active substance is preferably a pesticide or mixture of pesticides, whereby the pesticide or pesticide mixture is solid at ambient temperature and substantially insoluble in water. The melting point of the active substance is preferably above 25° C. The particulate active substance remains solid in the coating process which is described below, i.e. the active substance does not melt during preparation of the coated microparticles.

The term pesticide is understood to encompass herbicides, insecticides, acaricides, nematicides, ectoparasiticides and fungicides. Examples of compound classes to which the pesticide in the practise of the invention may belong include ureas, triazines, triazoles, carbamates, phosphoric acid esters, dinitroanilines, morpholines, acylalanines, pyrethroids, benzilic acid esters and polycyclic halogenated hydrocarbons.

Specific examples of pesticides suitable for the coating process according to the invention are listed below (common names from The Pesticide Manual, 9th Edition, British Crop Protection Council):

Ureas
  Chlorbromuron, Chloroxuron, Chlorotoluron, Fluometuron, Thiazafluron and Triasulfuron.
Haloacetanilides
  Dimethachlor, Alachlor, Propachlor.
s-Triazines
  Atrazine, Propazine, Terbuthylazine, Ametryn, Aziprotryne, Cyromazine.
Triazole derivatives
  Etaconazole, 1-[2-(2,4-dichlorophenyl)-pent-1-yl]-1H-1,2,4-triazole, Triadimefon, Difenoconazole.
Carbamates
  Dioxacarb, Aldicarb, Benomyl.
Phosiphoric acid ester
  Methidathion, Anilofos, Azinphos methyl, Fenamiphos, Azamethiphos.
Dinitroanilines
  Benfluralin, Pendimethalin, Butralin, Fluchloralin.
Acylalanines
  Metalaxyl, Fluralaxyl, Benzoylprop ethyl, Flamprop methyl.
Pyrethroids
  Cypermethrin, Resmethrin, Tetramethrin.
Benzilic acid esters
  Bromopropylate, Chlorobenzilate, Chloropropylate.
Miscellaneous
  Bromoxynil, Ioxynil, Oxadiazon, Dicofol, Fenoxycarb.
  Preferred pesticides are Chlorotoluron and Atrazin.

Each discrete coating layer around the particulate active substance is formed from the same polymeric material. Suitable polymers are well known in the art. Suitable polymeric materials in the practise of the invention can be structurally crosslinked polymers which are derived from aldehydes and phenols, ureas or melamines. Examples are phenol/formaldehyde resins, urea/formaldehyde resins and melamine/formaldehyde resins.

Preferred polymer coating layers are those which are biodegradable e.g. melamine/formaldehyde polymers, urea-formaldehyde polymers, polyurea, polyalkylglycols, polylactides, polyglycolides, natural polymers and mixtures of at least two of these polymers. Melamine/formaldehyde is most preferred. The molar ratio of melamine to formaldehyde can be between 1:2 and 1:8 and is preferably from 1:3 to 1:5.

Another object of the invention is a process for the preparation of coated microparticle agglomerates by forming an aqueous suspension, emulsion or solution A of a polymer or polymer-forming precursor, combining said suspension, emulsion or solution with powder active substance, and either ai) stirring the suspension, emulsion or solution A at high speed, and partially or wholly precipitating the polymer or polymer precursor on the microparticle surfaces and polymerising the polymer precursor, aii) isolating the suspension of coated microparticles, and aiii) dispersing the coated particles in the aqueous suspension, emulsion or solution A under low-speed stirring to form agglomerates, or bi) stirring the suspension, emulsion or solution at low speed to form clusters, bii) isolating the suspension of coated clusters, and biii) dispersing the coated clusters in the aqueous suspension, emulsion or solution A under high-speed stirring to form agglomerates, c) optionally repeating steps bii) and biii) after step aiii) or biii), and d) isolating the coated agglomerates.

FIG. 1 illustrates agglomerates prepared according to process variant a).

Precipitation procedures depend in general on the nature of the polymers or polymer precursors used in the process. If polymer and/or precursor is dissolved in solvent, precipitation is effected for example in removing at least partially the solvent or in adding a non-solvent for the polymer of precursor. Precipitation may also be effected in changing the pH value, e.g. by acidification of the aqueous suspension, emulsion or solution. Precipitation of polymers may also be effected by interfacial polymerisation in adding a co-reactant to the precursor suspension, emulsion or solution.

Powder active substance is understood to include amorphous and crystalline forms.

As a general rule the rotation speed of the stirrer under high-speed stirring is typically from 3 to 16 m/sec, preferably from 4 to 8 m/sec, measured at the farthest point to the axis of rotation of the stirrer. The rotation speed of the stirrer under low-speed stirring is typically between 0.5 and 3 m/sec, preferably between 1 and 2 m/sec, The isolation in steps aii), bii) and d) can be done by known methods, e.g. filtration, centrifugation or evaporation of moisture. After step d) it may be advantageous to dry the agglomerates to obtain an improved surface quality.

The agglomerates may be coated as a mixture of active substances or mixed after coating.

A safener may be included in the coated agglomerate mixture and may be coated together with the active substance or added after coating. The agglomerates may consist of coated safener particles and biologically active substance particles. It may be advantageous to include other additives in the mixture before or after coating, e.g. inert fillers, stabilisers, pigments, dyes, bait and repellants.

Another object of the invention is a composition containing discretely coated microparticle agglomerates as active substances which composition may be dry, e.g. in powder form, or in the form of an aqueous dispersion.

The agglomerate composition may be stored in a container prior to use. It may be advantageous to store the dry composition in a water-soluble bag or carton.

A further object of the invention is a method of treating plant growth deficiencies, pest attack in plants or animals, or nutrient-deficient soil by applying to the plant or animal locus a pesticidally and/or nutritionally effective amount of agglomerated particulate active substance according to the invention or a composition comprising a mixture of active substances.

Other possible uses of the coated agglomerated microparticles according to the invention are in water-treatment and hygiene.

The advantages of the coated microparticle agglomerates according to the invention are as follows:

a) compositions of coated microparticle agglomerates display more constant release rates of active substance (s);

b) there is a reduction in active substance necessary per unit area treated;

c) the active substance(s) can be mixed before or after coating;

d) the effectiveness of the active substance can be extended;

e) handling by users is safer than that of incompletely-coated particles, leading to reduced toxicological risk;

f) biologically degradable coatings can be used in agricultural applications;

g) contamination and waste through residue formation are avoided;

h) storage-stable and sprayable dispersions may be prepared;

i) the amount of coating material needed is reduced; and j) leaching is reduced.

The Examples below illustrate the invention in more detail. The measurement of release of the active substance is carried out as follows:

In order to provide ideal conditions under which the agglomerated particulate active substance can release by diffusion through the capsule walls, the test method is conducted under "sink conditions". The formulation is dispersed in 1 liter of an aqueous medium in an amount such that complete release of the active ingredient leads to a concentration in the solution of 10% of the solubility of the active ingredient. This dispersion is stirred gently without applying mechanical stress on the capsules. Filtered samples of the medium are taken at regular time intervals and analysed directly with respect to the active content by HPLC or GLC.

Since the active ingredient is only sparingly soluble in water, a mixture of buffer and surfactant solution in water can be used as release medium. The release medium used for chlorotoluron with a water solubility of 70 ppm can be for example a solution of 3% TWEEN-20 in dilute phosphate buffer pH 7. TWEEN-20, available commercially from ICI, is a nonionic surfactant comprising a sorbitan ester with 20 ethylene oxide units.

PREPARATIVE EXAMPLES

EXAMPLE 1 illustrates a known method with an encapsulation part of 22 weight %

12.5 g chlorotoluron are dispersed in 50 ml water. To this dispersion are added 15.5 ml of a 50 weight-% aqueous solution of a melamine(M)-formaldehyde(F) prepolymer (M:F molar ratio 1:3) partially etherified with methanol, and a suspension formed using low speed stirring. While maintaining the same stirring speed, the suspension is heated to 60° C. and 7.0 ml 2N citric acid are added. The suspension is stirred for a further 2 hours, cooled to room temperature and filtered. The filter cake is washed with 50 ml water and vacuum-dried at 60° C. There results a fine white powder of agglomerates with median particle diameter 2 to 120 μm.

The median particle diameter (MPD) is measured by laser light diffraction using a Cilas Granulometer.

EXAMPLE 2 inventive process with an encapsulation part of 22 weight % 12.5 g chlorotoluron are dispersed in 50 ml water. To this dispersion are added 10.5 ml of a 50 weight-% aqueous solution of a melamine (M)-formaldehyde (F) prepolymer (M:F molar ratio 1:3) partially etherified with methanol, and a suspension formed using a high-speed dissolver stirrer. While maintaining the same stirring speed, the suspension is heated to 60° C. and 7.0 ml 2N citric acid are added. The suspension is stirred for another hour, cooled to room temperature and filtered. Then the filtercake is added to a solution of 50 ml water and 5 ml of the 50 weight-% M/F-resin solution using low-speed stirring. While maintaining the same stirring speed, this suspension is heated to 60° C. and 7.0 ml 2N citric acid are added. The suspension is stirred for a further 2 hours, cooled to room temperature and filtered. The filter cake is washed with 50 ml water and vacuum-dried at 60° C. There results a fine white powder of agglomerates with median particle diameter of 10 to 30 μm.

EXAMPLE 3 inventive process with an encapsulation part of 30 weight % The procedure is followed as for Example 2 but in the second encapsulation step 10.5 ml of the 50 weight-% M/F resin aqueous solution are added. There results a fine white powder of agglomerates with median particle diameter of 10 to 50 μm.

APPLICATION EXAMPLES

The release characteristics of the agglomerates prepared in the above Examples are illustrated graphically on FIG. 2 by graphs 1, 2 and 3 corresponding to Examples 1, 2 and 3 respectively. The graphs in FIG. 2 show % release of active ingredient plotted against time in hours.

What is claimed is:

1. Encapsulated biologically active solid microparticle agglomerates, each agglomerate comprising either

I i) at least two closely associated microparticles, each microparticle being coated partially or completely by at least one discrete layer of a polymer, and ii) at least one outer discrete coating layer of the same polymer which envelops the coated microparticles to form an agglomerate of closely associated microparticles, or

II i) a cluster of at least two closely associated microparticles, each microparticle being coated partially or completely by at least one layer of a polymer, the microparticles adhering together through the polymer to form said cluster, and ii) at least one outer discrete coating layer of the same polymer which envelops said cluster to form a discrete agglomerate, wherein in types I and II an inter-phase boundary is formed between each particle and the first coating layer, between individual coating layers and between the outer agglomerating envelope layer and the penultimate coating layer, and the total weight of polymer coating within and outside the agglomerate is no greater than 40% of the average agglomerate weight.

2. Agglomerates according to claim 1, wherein the median particle diameter is between 3 and 2000 μm.

3. Agglomerates according to claim 1, wherein the weight of coating material around the microparticles and the agglomerate itself is from 5 to 40% of the agglomerate weight.

4. Agglomerates according to claim 1, wherein each agglomerate is a singly- or doubly-coated cluster of coated microparticles.

5. Agglomerates according to claim 1, wherein the active substance represents from 60 to 95% by weight of the coated agglomerate.

6. Agglomerates according to claim 1, wherein the biologically active substance is a pesticide or mixture of pesticides, whereby the pesticide or pesticide mixture is solid at ambient temperature and substantially insoluble in water.

7. Agglomerates according to claim 6, wherein the active substances are herbicides, insecticides, acaricides, nematicides, ectoparasiticides or fungicides.

8. Agglomerates according to claim 6, wherein the active substances are Chlorotoluron or Atrazin.

9. Agglomerates according to claim 1, wherein the polymer coating layers are melamine-formaldehyde polymers, urea-formaldehyde polymers, polyurea, polyalkylglycols, polylactides, polyglycolides, natural polymers or mixtures of at least two of these polymers.

10. A process for the preparation of coated microparticle agglomerates according to claim 1, by forming an aqueous suspension, emulsion or solution A of a polymer or polymer-forming precursor, combining said suspension, emulsion or solution with powder active substance, and either ai) stirring the suspension, emulsion or solution A at high speed, and partially or wholly precipitating the polymer or polymer precursor on the microparticle surfaces and polymerising the polymer precursor, aii) isolating the suspension of coated microparticles, and aiii) dispersing the coated particles in the aqueous suspension, emulsion or solution A under low-speed stirring to form agglomerates, or bi) stirring the suspension, emulsion or solution A at low speed to form clusters, bii) isolating the suspension of coated clusters, and biii) dispersing the coated clusters in the aqueous suspension, emulsion or solution A under high-speed stirring to form agglomerates, c) optionally repeating steps bii) and biii) after step aiii) or biii), and d) isolating the coated agglomerates.

11. A composition containing discretely coated microparticle agglomerates according to claim 1 which composition is dry or in the form of an aqueous dispersion.

12. A method of treating plant growth deficiencies, pest attack in plants or animals, or nutrient-deficient soil by applying to the plant or animal locus a pesticidally and/or nutritionally effective amount of agglomerated particulate active substance or a composition comprising a mixture of active substances.

* * * * *